United States Patent [19]

Lunkenheimer et al.

[11] Patent Number: 4,596,885
[45] Date of Patent: Jun. 24, 1986

[54] PROCESS FOR THE PREPARATION OF PHENYLGLYOXYLIC ACID ESTERS

[75] Inventors: Winfried Lunkenheimer; Andreas Wittig; Wilfried Draber; Helmut Timmler, all of Wuppertal, Fed. Rep. of Germany

[73] Assignee: Bayer Aktiengesellschaft, Leverkusen, Fed. Rep. of Germany

[21] Appl. No.: 875,707

[22] Filed: Feb. 6, 1978

[30] Foreign Application Priority Data

Feb. 25, 1977 [DE]  Fed. Rep. of Germany ....... 2708189

[51] Int. Cl.$^4$ ............................................. C07C 69/76
[52] U.S. Cl. ..................................... 560/51; 544/182; 560/23; 560/34; 560/53; 564/129; 564/163
[58] Field of Search ............................. 560/51, 53, 23

[56] References Cited

U.S. PATENT DOCUMENTS

| | | | |
|---|---|---|---|
| 3,553,258 | 1/1971 | Kaiser et al. | 560/23 |
| 3,754,006 | 8/1973 | Siggins | 560/51 |
| 3,979,430 | 9/1976 | Nelson et al. | 560/51 |
| 4,069,252 | 1/1978 | Findeisen et al. | 560/51 |
| 4,234,739 | 11/1980 | Photis | 560/51 |

OTHER PUBLICATIONS

March, *Advanced Organic Chem.: Reactions, Mechanisms & Structure*, p. 664 (1968).
Wagner et al, Synthetic Organic Chemistry, pp. 485–486 (1953).
Houben–Weyl, Methoden der Organischen Chemie, pp. 536–538, vol. VIII, (1952).
Smith et al, J.A.C.S. 71, pp. 3772–3773, (1949).
Angew, Chemie, 68, pp. 425–433 (1956).
Kimball, Organic Syntheses II, pp. 284–286 (1943).
Claisen, B., 10, pp. 429–431; and 844–848, (1877).
Groggins, Unit Processes in Organic Synthesis, 4th Ed., pp. 598–600 and 628, (1952).
Beilutein's Handbach der Organischen Chemie, 4th Ed., System #1289, from this page & pp. 659–660, Von Springer, Berlin, Germany.

*Primary Examiner*—Paul J. Killos
*Attorney, Agent, or Firm*—Sprung Horn Kramer & Woods

[57] ABSTRACT

A process for the preparation of a phenylglyocylic acid ester of the formula

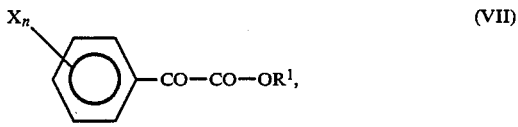

wherein
  $R^1$ represents alkyl,
  X represents halogen, alkyl, halogenoalkyl, alkoxy or nitro, and
  n represents 0, 1, 2, or 3 by contacting a benzoyl cyanide of the formula

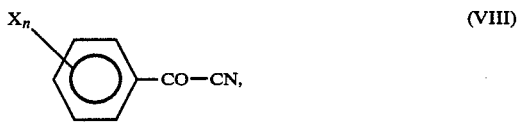

wherein X and n have the meanings stated above, in a sulphuric acid/water system in the presence of chloride ions at a temperature between 0° and 70° C. to form phenylglyoxylic acid amide and reacting the phenylglyoxylic acid amide without isolation with an alcohol of the formula $R^1$-OH, wherein $R^1$ has the meaning stated above, optionally in the presence of a diluent, at a temperature between 40° and 100° C.

18 Claims, No Drawings

PROCESS FOR THE PREPARATION OF PHENYLGLYOXYLIC ACID ESTERS

BACKGROUND OF THE INVENTION

1. Field of the Invention

The present invention relates to a process for the preparation of certain phenylglyoxylic acid esters (some of which are known and others of which are new), which can be used as intermediates for the synthesis of herbicidally active compounds.

2. Discussion of the Prior Art

It has already been disclosed in Angewandte Chemie 68, 430 (1956) that phenylglyoxylic acid esters (I), for example phenylglyoxylic acid methyl ester or phenylglyoxylic acid ethyl ester, are obtained in accordance with equation 1 below when benzoyl cyanide (II) is hydrolyzed with a concentrated mineral acid such as, in particular, with concentrated hydrochloric acid. See also Berichte der deutsch chem. Gesellschaft 10, 429 and 844 (1877) and Organic Synthesis 24, 16 (1944). The phenylglyoxylic acid (III) thereby formed is isolated and esterified with an alcohol in the presence of a mineral acid, for example hydrochloric acid, sulphuric acid or p-toluenesulphonic acid. See Berichte der deutsch Chem. Gesellschaft 12, 629 (1879); J. Org. Chem. 29, 278 (1964); Chem. Abstracts 74, 99 587j (1971) and U.S. Pat. No. 3,754,006.

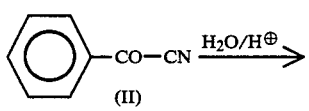

(II)

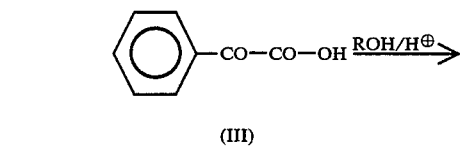

(III)

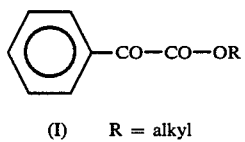

(I)   R = alkyl

However, this process has a number of disadvantages. Thus, with respect to the benzoyl cyanide, it is a two-stage process. In the first stage, that is to say the hydrolysis of benzoyl cyanide, considerable amounts of benzoic acid are always formed, in particular when acids which are not sufficiently concentrated are used (see Angewandte Chemie 68, 430 (1956)). The total yields are only between 35 and 70%. The proportion of by-products, in particular benzoic acid esters, of up to 20% is accordingly very considerable. In addition, very long reaction times are required. When the process is applied on a laboratory scale the reaction times are between 12 and 20 hours.

Moreover, it is also known that carboxylic acid esters (IV) are obtained in accordance with equation 2 below from nitriles (V) in a "one-pot process" when the latter are converted, with alcoholic hydrochloric acid, into imide-ester hydrochlorides (VI), which are then easily hydrolysed by water into carboxylic acid esters and ammonium chloride (see Houben-Weyl, Methoden der organischen Chemie (Methods of Organic Chemistry), Georg Thieme Verlag Stuttgart 1952, volume VIII, page 536 et seq.).

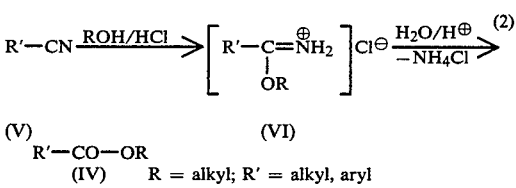

(V)   (VI)
R'—CO—OR
(IV)   R = alkyl; R' = alkyl, aryl

However, this process, which is in itself very appropriate for the preparation of carboxylic acid esters, cannot be applied to the preparation of phenylglyoxylic acid esters, that is compounds of the formula (IV), in which R' is a benzoyl radical, or of the formula (VII) below. If benzoyl cyanides, that is compounds of the formula (V), in which R' is a benzoyl radical, or of the formula (VIII) below, are used as starting materials, the reaction does not take the desired course. Rather, benzoyl cyanides decompose with alcohols in an acid medium into benzoic acid esters and hydrocyanic acid (see Angew. Chemie 68, 430 (1956)).

SUMMARY OF THE INVENTION

The present invention now provides a process for the preparation of a phenylglyoxylic acid ester of the general formula

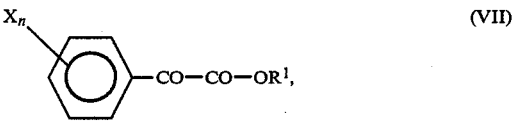

in which
R$^1$ represents alkyl,
X represents halogen, alkyl, halogenoalkyl, alkoxy or nitro and
n represents 0, 1, 2 or 3,
in which a benzoyl cyanide of the general formula

in which
X and n have the meanings stated above, is first hydrolysed in a sulphuric acid/water system in the presence, as a catalyst, of chloride ions at temperatures between 0° and 70° C. and the phenylglyoxylic acid amide thereby formed is reacted, without isolation, with an alcohol of the general formula

R$^1$—OH   (IX), in which R$^1$ represents alkyl, optionally in the presence of a diluent, at temperatures between 40° and 100° C.

In view of the state of the art, it is to be described as decidedly surprising that it is possible, under the conditions of the process according to the invention, to convert benzoyl cyanides into very pure phenylglyoxylic acid esters, with a high yield, in a manner which is industrially simple.

The process according to the invention has a number of advantages. Thus, with respect to the benzoyl cyanide, it is a one-stage process ("one-pot process") and the yields of about 90% are very high. At the same time, the proportion of by-products is very small. The phenylglyoxylic acid esters, which are isolated by vacuum distillation, can therefore be employed immediately, without further purification, for subsequent reactions. Since, in addition, the overall reaction time is very short—when the process is applied on a laboratory scale it is between 2 and 4 hours—the process according to the invention is substantially more economical than the known processes.

If benzoyl cyanide is used as the starting material, sodium chloride is used as the catalyst and methanol is used as the alcohol, the course of the reaction can be represented by the following equation:

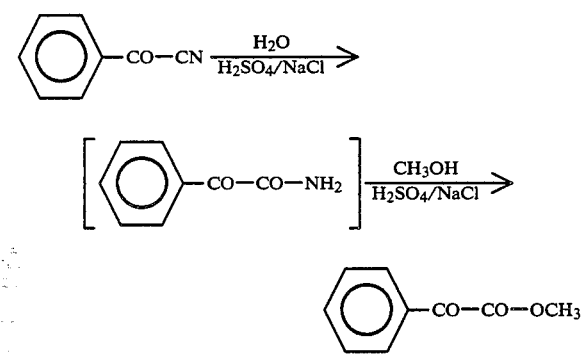

The formula (VIII) provides a general definition of the benzoyl cyanides to be used as starting materials. In this formula, X preferably represents halogen, in particular fluorine, chlorine and bromine; alkyl or alkoxy with 1 to 4 carbon atoms in each case; halogenomethyl, in particular trichloromethyl, difluorochloromethyl or trifluoromethyl; or the nitro group. The index n preferably represents 0, 1 or 2. Examples of the benzoyl cyanides (VIII) which may be mentioned are: benzoyl cyanide, 4-chlorobenzoyl cyanide, 3-chlorobenzoyl cyanide, 3-trifluoromethylbenzoyl cyanide, 3-methylbenzoyl cyanide, 4-methylbenzoyl cyanide, 4-butylbenzoyl cyanide, 4-methoxybenzoyl cyanide, 3,4-dimethoxybenzoyl cyanide, 4-nitrobenzoyl cyanide, 4-fluorobenzoyl cyanide and 3-methoxybenzoyl cyanide.

The formula (IX) provides a general definition of the alcohols which are also to be used as starting materials. In this formula, R' preferably represents straight-chain or branched alkyl with 1 to 4 carbon atoms. Examples which may be mentioned are: methanol, ethanol, isopropanol, isobutanol, n-propanol and n-butanol.

The benzoyl cyanides of the formula (VIII) and the alcohols of the formula (IX) are compounds which are known generally in organic chemistry.

The reaction according to the invention can be carried out in the absence or in the presence of an organic diluent which is inert under the reaction conditions. Such diluents which can be used are, in particular, benzoic acid esters, for example benzoic acid ethyl ester or benzoic acid methyl ester.

The reaction according to the invention is carried out in the presence of chloride ions as a catalyst. For this, one can employ all the compounds which donate chloride ions and which can be customarily used, such as, in particular, acetyl chloride, hydrochloric acid, sodium chloride, ammonium chloride or benzoyl chloride. The chlorides of other alkali metals or of the alkaline-earth metals, other organic acid chlorides and other chlorine bearing inorganic acids are also useful.

The hydrolysis in the process according to the invention is carried out between 0° and 75° C., preferably between 20° and 50° C., and the ester-forming reaction is carried out at temperatures between 40° and 100° C., preferably between 40° and 80° C.

In carrying out the process according to the invention, preferably 1 to 3 moles of sulphuric acid, 1–3 moles of water, 0.01 to 0.2 mole of chloride catalyst and 2 to 5 moles of alcohol are employed per mole of benzoyl cyanide of the formula (VIII). The phenylglyoxylic acid esters of the formula (VII) are isolated in the generally customary manner.

Most of the phenylglyoxylic acid esters of the formula (VII) which can be prepared according to the invention are known. They can be used, for example, as intermediates in the synthesis of herbicidally active compounds. For example, the compound 4-amino-3-methyl-6-phenyl-1,2,4-triazin-5(4H)-one can be obtained from phenylglyoxylic acid methyl ester (VIIA) according to the following equation (see German Offenlegungsschrift (DOS No. 2,224,161):

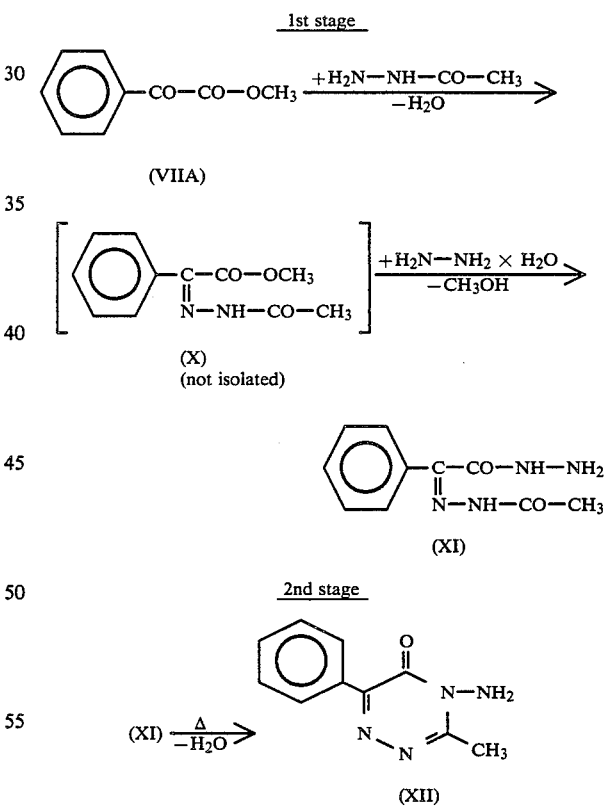

In detail, the above synthesis may be carried out as follows.

1st stage 1 mole of phenylglyoxylic acid methyl ester (VIIA) and 1 mole of acetylhydrazine in 780 g of isopropanol were heated under reflux for 5 hours. A little p-toluenesulphonic acid was added as a catalyst. The hdyrazone (X) was obtained as an isomer mixture, one isomer crystallising. The mixture was therefore reacted further without isolating the hydrazone. After the ester had been consumed, hydrazine hydrate was added to this reaction solution and the mixture was kept at 20° C. for 5 hours, whilst stirring. Thereafter, the reaction mixture was cooled to 0° to 5° C. and the product was filtered off. The yield of pure hydrazide (XI) was 85%.

2nd stage 1,000 g of isopropanol were added to 1 mole of the hydrazide (XI) and the mixture was stirred for 24 hours at 100° C. in a closed kettle (1–2 atmospheres gauge). The product was then filtered off at −5° C. 4-Amino-3-methyl-6-phenyl-1,2,4-triazin-5(4H)-one (XII) of melting point 167°–169° C. was obtained in 83% yield.

The process of the present invention is illustrated by the following preparative Examples.

EXAMPLE 1

(a) According to the invention

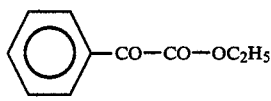
(VIIB)

On a laboratory scale 13.1 g (0.1 mol) of benzoyl cyanide were added dropwise, at 40° C., to a mixture of 5.35 g (0.1 mol) of ammonium chloride, 5.4 g (0.3 mol) of water, 19.7 g (0.2 mol) of concentrated hydrochloric acid and 10.2 g (0.1 mol) of concentrated sulphuric acid. The mixture was stirred for 3 hours at 40° C., 13.8 g (0.3 mol) of ethanol were then added and the mixture was stirred for 3.5 hours at 75° C. After cooling, the reaction mixture was extracted by stirring with 100 ml of ethylene chloride and the organic phase was washed with water and sodium bicarbonate solution, dried over sodium sulphate and evaporated. This gave 15.5 g (85% of theory) of phenylglyoxylic acid ethyl ester, which was in the form of a light yellow oil and had a purity of 98% (determined by gas chromatography) and a boiling point of 98°–102° C./0.4 mm Hg.

(b) According to the state of the art (comparison example)

(i) Hydrolysis with concentrated hydrochloric acid; esterification in the presence of concentrated sulphuric acid 13.1 g (0.1 mol) of benzoyl cyanide were stirred with 70 ml of concentrated hydrochloric acid for 18 hours at 50° C. After cooling, the mixture was poured into 300 ml of water and extracted with chloroform, the extract was dried over sodium sulphate and evaporated and the residue was distilled in vacuo. This gave 7.0 g (47% of theory) of phenylglyoxylic acid of boiling point 138°–141° C./12 mm Hg. The distillate soon solidified and could be recrystallised from ligroin (melting point 64.5°–65.5° C.).

A mixture of 900 g (6 mol) of phenylglyoxylic acid, 4 liters of ethanol and 30 ml of concentrated sulphuric acid was stirred under reflux for 8 hours, cooled and filtered and the filtrate was evaporated. The residue was taken up in ether, the ether solution was washed with water and sodium bicarbonate solution, dried over sodium sulphate and evaporated and the residue was distilled in vacuo. This gave 810 g (76% of theory) of phenylglyoxylic acid ethyl ester, which had a boiling point of 92° C./0.15 mm Hg and a purity of 95% (determined by gas chromatography).

(ii) Hydrolysis and esterification in the presence of 30% strength hydrochloric acid 13.7 g (0.1 mol) of benzoyl cyanide were added dropwise, at 40° C., to a mixture of 29.6 g (0.3 mol) of concentrated hydrochloric acid and 6.7 g of water (corresponding to 30% strength hydrochloric acid), and the mixture was stirred for 2 hours at this temperature.

It could be established by thin-layer chromatography that the desired reaction did not proceed, but that hydrolysis to benzoic acid gradually occurred.

EXAMPLE 2

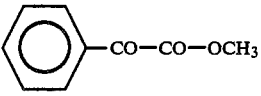
(VIIA)

On a laboratory scale

A mixture of 393 g (3 mol) of benzoyl cyanide, 20.3 g (0.26 mol) of acetyl chloride and 202 g of benzoic acid methyl ester was added dropwise, at 22° C., to 450 g (4.6 mol) of concentrated sulphuric acid. The mixture was subsequently stirred for one hour and 72 g (4 mol) of water were then added at 22° C. in the course of about 20 minutes. The mixture was then stirred for a further 3 hours at 22° C. 304 g (9.5 mols) of methanol were added to the reaction mixture and the mixture was stirred for 3 hours at about 70° C. After cooling, the reaction mixture was diluted with 390 g of water. The organic phase was separated off and washed successively with 160 g of water, 160 g of sodium bicarbonate solution and 160 g of water. The combined aqueous phases were extracted twice with 30 ml of toluene each time. The organic phases were combined, and concentrated by distilling off the solvent. Distillation of the residue gave 473 g (96% of theory) of phenylglyoxylic acid methyl ester, which had a boiling point of 136° C./12 mm Hg and a purity of 99% (determined by gas chromatography).

On a semi-industrial scale

A solution of 113.2 g (1.935 mol) of sodium chloride in 348.0 g (19.35 mol) of water and 1,935 g (19.35 mol) of sulphuric acid was warmed to 45° C. 2.535 g (19.35 mol) of benzoyl cyanide were added dropwise, at 40°–45° C., to this solution in the course of about 3.5 hours, whilst cooling slightly. After the reaction (slightly exothermic) had started, the temperature was controlled by regulating the dropping rate and the water-cooling. After the dropwise addition had ended, the mixture was subsequently stirred for 1 hour, the temperature being kept at about 45° C. Thereafter, 1,850 g (58 mol) of methanol were added and the mixture was heated to 75° C. for 3 hours. It was left to stand overnight, excess methanol was distilled off at a bath temperature of 120° C., the mixture was cooled to 70° C. and 1,000 ml of water were added. The organic phase was separated off, dried over sodium sulphate and distilled. This gave 2,890 g (86.5% of theory) of phenylglyoxylic acid methyl ester, which was in the form of a light yellow oil and had a boiling point of 82°–85°

C./0.5 mm Hg and a purity of 96% (determined by gas chromatography).

It will be understood that the specification and examples are illustrative but not limitative of the present invention and that other embodiments whithin the spirit and scope of the invention will suggest themselves to those skilled in the art.

What we claim is:

1. A process for the preparation of a phenylglyoxylic acid amide of the formula

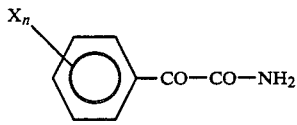

wherein

X represents halogen, alkyl, halogenoalkyl, alkoxy or nitro, and n represents 0, 1, 2 or 3, which comprises:

hydrolyzing a benzoyl cyanide of the formula

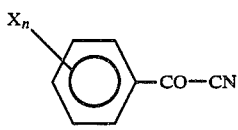

wherein X and n have the meanings stated above, in a sulphuric acid/water system in the presence of chloride ions at a temperature between 0° and 75° C.

2. A process according to claim 1 wherein the hydrolysis is carried out at a temperature between 20° and 50° C.

3. A process according to claim 1 wherein ammonium chloride, sodium chloride or hydrogen chloride is employed to supply the chloride ions.

4. A process according to claim 1 wherein benzoyl chloride or acetyl chloride is employed to supply the chloride ions.

5. A process according to claim 1 wherein X represents fluorine, chlorine, bromine, alkyl of 1 to 4 carbon atoms, alkoxy with 1 to 4 carbon atoms, trifluoromethyl, difluorochloromethyl, trichloromethyl or nitro, and n is 0, 1 or 2.

6. A process according to claim 1 wherein said cyanide is selected from the group consisting of benzoyl cyanide, 4-chlorobenzoyl cyanide, 3-chlorobenzoyl cyanide, 3-trifluoromethylbenzoyl cyanide, 3-methylbenzoyl cyanide, 4-methylbenzoyl cyanide, 4-tert.-butylbenzoyl cyanide, 4-methoxybenzoylcyanide, 3,4-dimethoxybenzoyl cyanide, 4-nitrobenzoyl cyanide, 4-fluorobenzoyl cyanide and 3-methoxybenzoyl cyanide.

7. A process according to claim 6 wherein said cyanide is benzoyl cyanide.

8. A process according to claim 1 wherein there are employed 1–3 mols of sulphuric acid, 1–3 mols of water, and 0.01–0.2 mols of chloride ions per mol of benzoyl cyanide.

9. An improved method for preparing glyoxylic acid amides which comprises:
    (a) reacting an acyl nitrile compound with concentrated sulfuric acid in the presence of halogen anion to form a first reaction product; and
    (b) reacting said first reaction product with water.

10. The method of claim 9 wherein said acyl nitrile compound is a benzoyl cyanide.

11. The method of claim 9 wherein said reaction with water effects precipitation of the glyoxamide of said acyl nitrile compound.

12. A method for preparing an arylglyoxylate from an aroyl nitrile compound which comprises the steps of:
    (a) reacting said aroyl nitrile compound with concentrated sulfuric acid in the presence of halogen anion and about an equimolar amount of an acylating agent based on the nitrile compound to form a first reaction product; and
    (b) reacting said first reaction product with an alcohol to form said arylglyoxylate; provided, however, that said alcohol is not a tertiary alcohol.

13. The method of claim 12 wherein said halogen anion is chloride.

14. The method of claim 12 wherein the reaction between said aroyl nitrile compound and said concentrated sulfuric acid is conducted in the presence of a solvent.

15. The method of claim 12 wherein said acylating agent is benzoyl chloride.

16. The method of claim 17 wherein said aroyl nitrile compound is a benzoyl cyanide and said alcohol is selected from the group consisting of methanol and ethanol.

17. The method of claim 12 wherein said acylating agent is acetyl chloride.

18. The method of claim 12 wherein the reaction between the aroyl nitrile compound and said concentrated sulfuric acid is conducted in the presence of a diluent.

* * * * *